US 011250564B2

(12) United States Patent
Brandl

(10) Patent No.: US 11,250,564 B2
(45) Date of Patent: Feb. 15, 2022

(54) METHODS AND SYSTEMS FOR AUTOMATIC MEASUREMENT OF STRAINS AND STRAIN-RATIO CALCULATION FOR SONOELASTOGRAPHY

(71) Applicant: GE Precision Healthcare LLC, Milwaukee, WI (US)

(72) Inventor: Helmut Brandl, Zipf (AT)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 151 days.

(21) Appl. No.: 16/721,036

(22) Filed: Dec. 19, 2019

(65) Prior Publication Data

US 2021/0192718 A1 Jun. 24, 2021

(51) Int. Cl.
| | | |
|---|---|---|
| G06T 7/00 | (2017.01) | |
| A61B 8/08 | (2006.01) | |
| A61B 8/00 | (2006.01) | |
| A61B 5/00 | (2006.01) | |
| G06T 7/11 | (2017.01) | |

(52) U.S. Cl.
CPC .......... *G06T 7/0012* (2013.01); *A61B 5/4331* (2013.01); *A61B 8/463* (2013.01); *A61B 8/485* (2013.01); *A61B 8/5207* (2013.01); *G06T 7/11* (2017.01); *G06T 2207/20084* (2013.01); *G06T 2207/30004* (2013.01)

(58) Field of Classification Search
CPC ............... G06T 7/0012; G06T 7/11; G06T 2207/30004; G06T 2207/20084; A61B 8/485; A61B 8/463; A61B 5/4331; A61B 8/5207

See application file for complete search history.

(56) References Cited

U.S. PATENT DOCUMENTS

| | | | |
|---|---|---|---|
| 2010/0134629 A1* | 6/2010 | Lindop | A61B 8/485 348/163 |
| 2011/0060222 A1* | 3/2011 | Thittai | G01S 7/52042 600/438 |
| 2016/0015365 A1* | 1/2016 | Li | A61B 8/5223 600/438 |
| 2017/0049416 A1* | 2/2017 | Azar | A61B 8/4455 |
| 2017/0086795 A1* | 3/2017 | Kanayama | A61B 8/5207 |
| 2019/0029651 A1* | 1/2019 | Patil | A61B 8/485 |
| 2019/0159762 A1* | 5/2019 | Li | G01S 7/52042 |

* cited by examiner

*Primary Examiner* — Emily C Terrell
*Assistant Examiner* — Molly Delaney
(74) *Attorney, Agent, or Firm* — McAndrews, Held & Malloy, Ltd.; Jacob Groethe; David Bates

(57) ABSTRACT

Systems and methods are provided for automatic measurement of strains and strain-ratio calculation for sonoelastography.

21 Claims, 5 Drawing Sheets

METHODS AND SYSTEMS FOR AUTOMATIC MEASUREMENT OF STRAINS AND STRAIN-RATIO CALCULATION FOR SONOELASTOGRAPHY

FIELD

Aspects of the present disclosure relate to medical imaging. More specifically, certain embodiments relate to methods and systems for automatic measurement of strains and strain-ratio calculation for sonoelastography, particularly using artificial intelligence (AI) algorithms.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

In some instances, medical imaging systems may be used to conduct particular types of examination. One such type in elastography based examination. Use of medical imaging systems in conjunction with such examination poses certain challenges, particularly with respect to assessing outcome of the examination. Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for automatic measurement of strains and strain-ratio calculation for sonoelastography, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
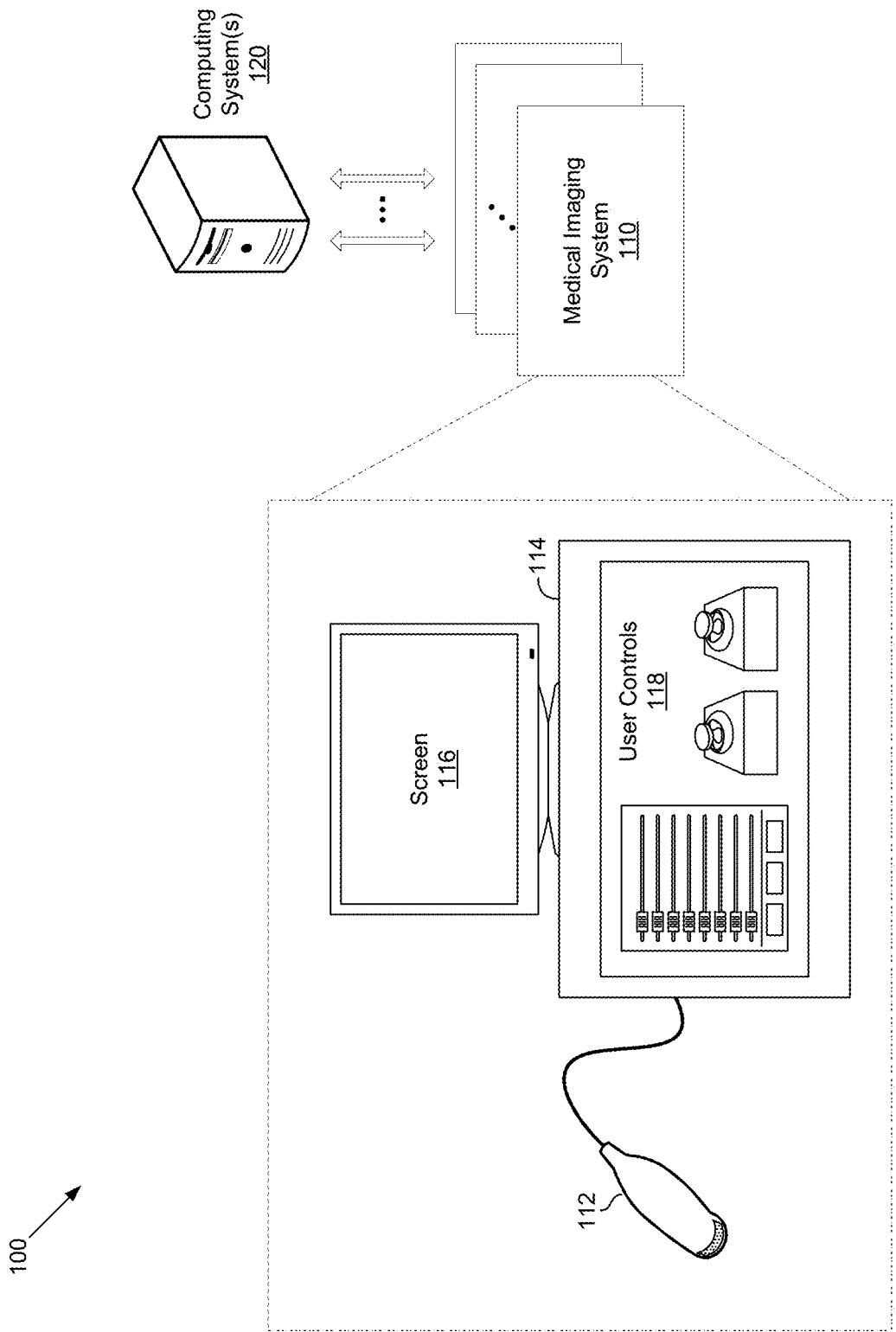
FIG. 1 is a block diagram illustrating an example medical imaging arrangement that may be configured for supporting automatic measurement of strains and strain-ratio calculation for sonoelastography.

Certain implementations in accordance with the present disclosure may be directed to automatic measurement of strains and strain-ratio calculation for sonoelastography. In particular, various embodiments have the technical effect of enhancing elastography based medical examinations by use of automatic measurement of strain values and strain-related determinations, such as based on strain-ratio calculations. Aspects of the present disclosure have the technical effect of allowing for increasing reliability and accuracy of outcomes of elastography based medical examinations by allowing for more accurate assessment of strain-related data that pertain to determining such outcomes.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIGS. 1 and 2.

Figure 2:
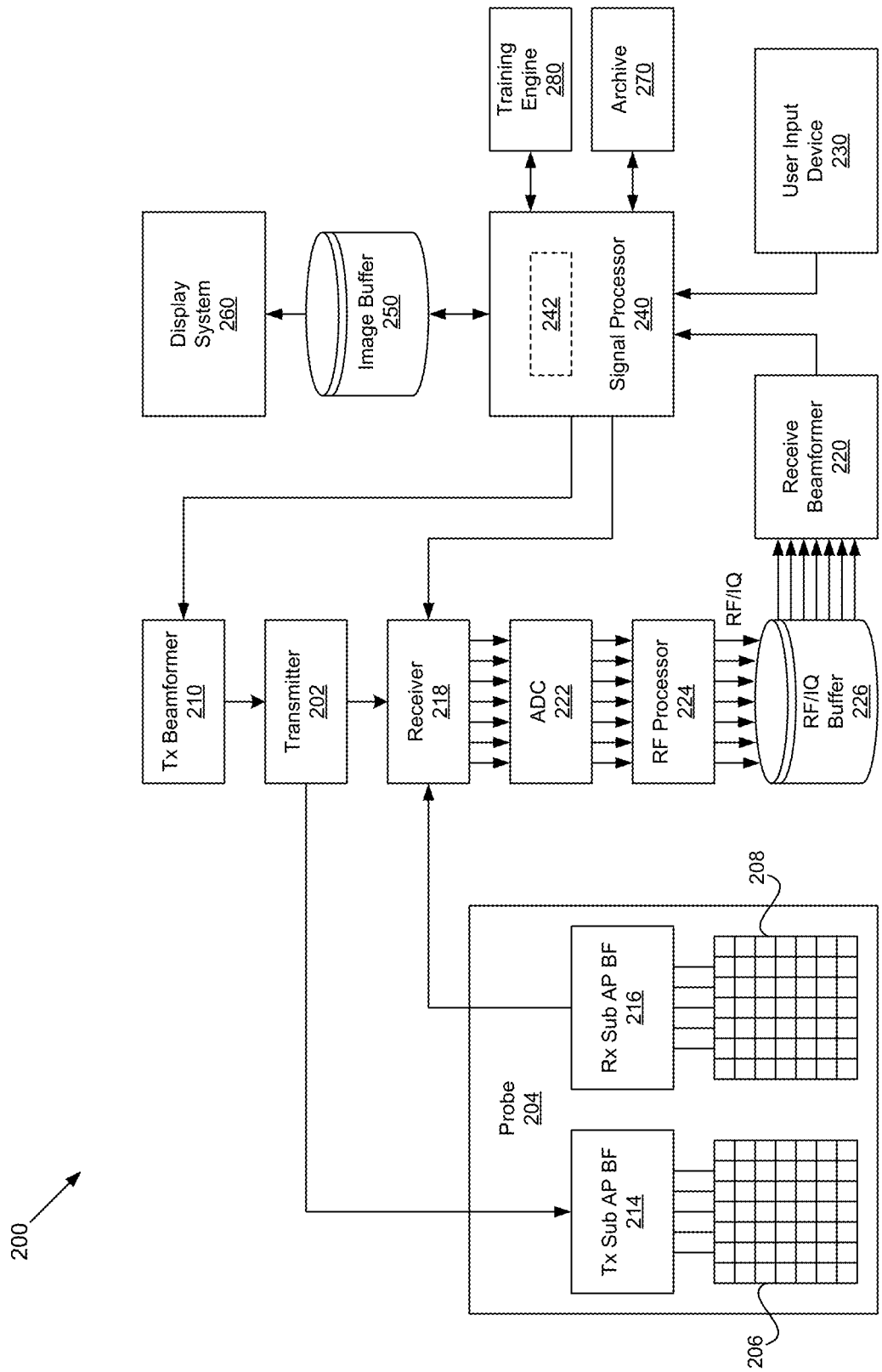
FIG. 2 is a block diagram illustrating an example ultrasound system that may be configured for supporting automatic measurement of strains and strain-ratio calculation for sonoelastography.

FIG. 1 is a block diagram illustrating an example medical imaging arrangement that may be configured for supporting automatic measurement of strains and strain-ratio calculation for sonoelastography. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 110 may be an ultrasound system, configured for generating and/or rendering ultrasound images. An example implementation of an ultrasound system, which may correspond to the medical imaging system 110, is described in more detail with respect to FIG. 2. As shown in FIG. 1, the medical imaging system 110 may comprise a scanner device 112, which may be portable and movable, and a display/control unit 114.

The scanner device 112 may be configured for generating and/or capturing particular type of imaging signals (and/or data corresponding thereto), such as by being moved over a patient's body (or part thereof), and may comprise suitable circuitry for performing and/or supporting such functions. The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost (by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110.

In some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other Cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In accordance with the present disclosure, medical imaging systems (e.g., the medical imaging system 110) may be configured for supporting automatic measurement of strains and strain-ratio calculations for sonoelastography. In this regard, medical imaging (e.g., ultrasound imaging) may be used in elastography related applications (referred to as sonoelastography in the context of ultrasound imaging), in which elastic properties and stiffness of soft tissue (e.g., of particular organ or body part) may be assessed and/or determined (e.g., mapped). In this regard, elastography may be used in cases where softness of soft tissue and changes therein (e.g., softening or hardening of the tissue) may have medical implications.

For example, elastography may be used to check for softening of the cervix in pregnant women. In this regard, softening of the cervix during pregnancy poses a serious risk for preterm delivery. Preterm softening of the cervix typically arises from the center of the cervical canal and is expanding from there until the entire cervix is affected. Thus, elastography (e.g., sonoelastography) of the cervix may show whether it is rigid and patent, or if softening started or has already occurred.

For example, sonoelastography may be performed in the form of endo-vaginal examination, in which applying strain elastography may demonstrate the condition of the cervix. In strain elastography clinicians may typically make a determination of the softness of the tissue (and thus whether softening of the cervix occurred or is occurring) based on assessment of strain and/or strain-ratios. In this regard, strain is a measure of deformation exhibited by a particular tissue (or area thereof) in response to pressure or stress applied thereto, and as such may be used as indicative of the softness of the tissue; a strain-ratio calculation measures the ratio of strains exhibited or measured for two different areas (corresponding to, e.g., different tissues and/or different parts of the same tissue), ideally when exposed to the same amount of stress. For example, during strain elastography external compression is applied to tissue, and ultrasound images before and after the compression are taken and compared, with the areas of the image(s) that are least deformed being the ones that are the stiffest (i.e., hardest), while the most deformed areas being the least stiff (softest). What may typically be displayed to the clinician during strain elastography is image of relative distortions (i.e., strains) in the examined tissues. Thus, in conventional solutions, clinicians' determination of softness of the tissue is typically based on visual examination of displayed images during the examination (medical imaging) to assess strain and/or strain-ratios.

When clinicians determine (or suspect) that softening of the cervix occurred or is occurring, the patient is typically referred for further examination. However, because the risks that softening of the cervix poses, as noted above, clinicians tend to be overly cautious, thus identifying most detected deformations (e.g., strains and/or strain-ratio) as suggesting softening of the cervix, which may lead to over-diagnosis. Therefore, increasing the reliability and precision of elastography of cervix is desirable.

Accordingly, in various implementations of the present disclosure, medical imaging systems may be configure to support automatic measurement of strains and strain-ratio calculation for sonoelastography, to allow for increasing reliability of the strain elastography, and thus reduce over-diagnosis (e.g., of such possible issues or problems as softening of the cervix). Further, in many implementations this may be done particularly by use of artificial intelligence (AI) algorithms, to perform and/or optimize such automatic measurements and/or calculations, and/or to further enhance related functions (e.g., setup and conduct of the examination, assessments, etc.). Use of automatic measurement of strains and strain-ratio calculation for sonoelastography, particularly in conjunction with cervical examinations, is described in more detail below.

In addition to enhancing the reliability of cervix examination, automatic measurement of strains and strain-ratio calculation may also be used for other pregnancy related applications. For example, in instances where the delivery does not begin and is induced by medication, automatic measurements of strains and strain-ratio calculations in sonoelastography may be used to check whether the cervix responded (or not) to the medication. Further, while various example implementations are described with respect to use of strain elastography in conjunction with cervical examinations, the disclosure is not limited only to such applications, and the solutions described herein (particularly with respect to use of automatic measurements of strains and strain-ratio calculations in sonoelastography, and specifically by means of AI-algorithms) may be similarly used in other applications where strain elastography is used, such as breast examinations (e.g., diagnosis imaging for lesions), small parts examinations (e.g., imaging of thyroid and testicular lesions), prostate examinations (e.g., ultrasound imaging for lesions), and the like.

FIG. 2 is a block diagram illustrating an example ultrasound system that may be configured for supporting automatic measurement of strains and strain-ratio calculation for sonoelastography. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1.

The ultrasound system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270.

For example, the user input device 230 may include button(s), rotary encoder(s), a touchscreen, motion tracking, voice recognition, a mouse device, keyboard, camera and/or any other device capable of receiving user directive(s). In certain embodiments, one or more of the user input devices 230 may be integrated into other components, such as the display system 260 or the ultrasound probe 204, for example. As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. Additionally and/or alternatively, the user input device 230 may include image analysis processing to identify probe gestures by analyzing acquired image data.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise a strain assessment module 242, which comprises suitable circuitry, interfaces, logic, and/or code that may be configured to perform and/or support various functions or operations relating to, or in support of automatic measurement of strains and strain-ratio calculation for sonoelastography, as described in more detail below.

In some implementations, the signal processor 240 (and/or components thereof, such as the strain assessment module 242) may be configured to implement and/or use artificial intelligence and/or machine learning techniques to enhance and/or optimize imaging related functions or operations. For example, the signal processor 240 (and/or components thereof, such as the strain assessment module 242) may be configured to implement and/or use deep learning techniques and/or algorithms, such as using deep neural networks (e.g., a convolutional neural network), and/or may utilize any suitable form of artificial intelligence image analysis techniques or machine learning processing functionality, which may be configured to analyze acquired ultrasound images, such as to identify, segment, label, and track structures (or tissues thereof) meeting particular criteria and/or having particular characteristics.

In an example implementation, the signal processor 240 (and/or components thereof, such as the strain assessment module 242) may be provided as a deep neural network, which may be made up of, for example, an input layer, an output layer, and one or more hidden layers in between the input and output layers. Each of the layers may be made up of a plurality of processing nodes that may be referred to as neurons. For example, the input layer may have a neuron for each pixel or a group of pixels from a scan plane of an anatomical structure. The output layer may have a neuron corresponding to a plurality of pre-defined structures or types of structures (or tissue(s) therein). Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The neurons of a fourth layer may learn characteristics of particular tissue types present in particular structures, etc. Thus, the processing performed by the deep neural network (e.g., convolutional neural network) may allow for identifying biological and/or artificial structures in ultrasound image data with a high degree of probability.

In some implementations, the signal processor 240 (and/or components thereof, such as the strain assessment module 242) may be configured to perform or otherwise control at least some of the functions performed thereby based on a user instruction via the user input device 230. As an example, a user may provide a voice command, probe gesture, button depression, or the like to issue a particular instruction, such as to control various aspects of automatic measurement of strains and strain-ratio calculation, and/or to provide or otherwise specify various parameters or settings relating thereto, as described in more detail below.

The training engine 280 may comprise suitable circuitry, interfaces, logic, and/or code that may be operable to train the neurons of the deep neural network(s) of the signal processor 240 (and/or components thereof, such as the strain assessment module 242). For example, the signal processor 240 may be trained to identify particular structures and/or tissues (or types thereof) provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images of particular structures to train the signal processor 240 (and/or components thereof, such as the strain assessment module 242) with respect to the characteristics of the particular structure(s), such as the appearance of structure edges, the appearance of structure shapes based on the edges, the positions of the shapes relative to landmarks in the ultrasound image data, and the like, and/or with respect to characteristics of particular tissues (e.g., softness thereof). In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, the ultrasound system 200 may be configured to support automatic measurement of strains and strain-ratio calculation for sonoelastography. In this regard, as noted above, elastography (e.g., sonoelastography) may be used in examining pregnant women for softening of the cervix, a condition that poses serious health risks (e.g., preterm delivery). For example, strain elastography (e.g., applied in the form of endo-vaginal examination) of the cervix may show whether the cervix is rigid and patent, or if softening starts or has already occurred. However, because of the serious risks that softening of the cervix poses, clinicians administering such examinations may tend to over-diagnose. This is further exacerbated by the fact that the examination is typically performed based on visual examination of displayed images by the clinicians, this may result in substantial number of cases where softening of the cervix is erroneously suspected and the patient is unnecessarily referred for further examination. As noted above, strain elastography may also be used in other applications (e.g., verifying response to medication for inducing delivery, breast examination (diagnosis for lesions), examination of certain small organs or body structures (imaging of thyroid and testicular lesions), prostate examination (ultrasound imaging for lesions), and the like). Similar issues as those noted with respect to strain elastography of the cervix may also arise in these other applications, in substantially similar manner—that is, over-diagnose by clinicians based on visual examination of the displayed images.

Some solutions have been proposed for trying to address some of these diagnose related problems. For example, clinical studies have been done for many of the elastography applications described above, and in many of these studies, cut-off values for the strain-ratio are proposed—that is, to define which strain-ratios may be indicative of issues. Nonetheless, such solutions do not address a main contributing factors in cases where misdiagnosis or over-diagnosis may occur—namely, the user-dependency of conventional solutions.

Solutions in accordance with the present disclosure address these issues, by simplifying workflow of the examination, decreasing user-dependencies, and expediting screening of images during examination. This may be done by incorporating automatic or semi-automatic approach for measuring strain and/or calculating strain-ratios, particularly using artificial intelligent (AI) techniques, to enhance reliability and accuracy of strain elastography. These solutions may be applied in any of the strain elastography applications noted above.

In various implementations, medical imaging systems (e.g., the system ultrasound system 200) may be configured to automatically measure strain and/or strain-ratio calculations during imaging operations. In this regard, rather than merely displaying images that reflect variations in strain characteristics in the imaged area, the medical imaging systems may be configured to measure the strain (e.g., in particular parts) and to provide strain related feedback to the user (e.g., clinician) to reduce ambiguity or uncertainty with respect to the results of the examination. For example, in some implementations, the medical imaging systems (e.g., the system ultrasound system 200) may be configured to allow the user to specify a particular area (e.g., by placing single region of interest (ROI) box over the area), and to provide automatic strain related measurement (and/or assessment based thereon) of that particular area. Such approach provides a fast and simple way to come to a clinical decision about the state of the examined tissue (or related structure/organ), and thus make better decisions about the next actions to be taken.

In cervical softening related use cases, for example, the user may only have to place a single ROI-box over the cervical canal area, and the system may then perform automatic softness assessment of cervical canal area—e.g., automatically performing measurement of strain, automatically determining the softest as well as the hardest regions based on the measured strains, and/or automatically performing the ratio measurements. In some instances, predefined data may be used during such automatic functions. For example, the strain measurement and/or stain-ratio calculation may be performed based on preprogrammed cut-off values (e.g., obtained from clinical studies or the like). In some instances, these values may be configurable, to allow operators to adjust any of these values (if necessary).

In some implementation, the system may be configured to enable the user to control various aspects or characteristics of the scan. For example, with respect to the ROI-box, in addition to controlling placement of the ROI-box (i.e., where to place it), the user may be able to control or adjust the size of the ROI-box (e.g., on the screen/display, by moving its edges to expand or shrink the box in particular direction, by setting minimum and/or maximum limits for the size of the ROI-box, etc.). In such implementations, where the user does not set or adjust the size of the ROI-box, the system may be configured to use pre-defined default size.

The measurements/calculations and assessments based thereon may be performed as part of imaging related processing, via suitable processing resources in the system. For example, in the ultrasound system 200, the signal processor 240 (and/or components thereof, such as the strain assessment module 242) may be configured to performed the automatic measurement of strains and strain-ratio calculation in the course of processing the received echoes, and signals and/or data based thereon. In this regard, in various implementations, artificial intelligence (AI) techniques and/or algorithms (e.g., using deep learning networks, as described above) may be used in performing and continually enhancing the automatic measurement of strains and strain-ratio calculation, and assessments based thereon. Example use scenarios are described with respect to FIGS. 3 and 4.

In an example use scenario, during strain elastography the tissue in the examined body part or area (e.g., cervix and surrounding area) may be compressed/decompressed manually using the ultrasound probe (e.g., using specialized probe or probe attachment for endo-vaginal examination in the case of strain elastography of the cervix). The compression/decompression produces strain in the tissue underneath the probe. The system may be automatically measure the, such as based on calculation based on speckle correlation of the signals of compressed vs. uncompressed tissue. In this regard, the measured strain values may be assigned based on a pre-defined range—e.g., between 0 and 2%, with 0% indicating no strain (i.e., no elasticity and no tissue deformation, thus signifying that the tissue is very hard), and 2% indicating very soft tissue (e.g., tissue is very elastic, easy to deform).

The measured strain values may be used by the system for making other strain-related determination and/or assessments based thereon. For example, the system may automatically calculate the mean strain value and/or strain ratio based on the measured strain values. In some instances, the measured strain values may be used to adjust or otherwise controlled the displaying of images. For example, different colors (and hues thereof) may be used to signify soft and/or hard tissue areas—e.g., in non-limiting implementation, tissue areas with higher strain values (softer) may be colored red (with increasing color saturation), and tissue areas with lower strain values (harder) are colored blue (with increasing color saturation). The system may also be configure to provide feedback relating to the measured strain values, and/or determinations and/or assessments based thereon. For example, the strain-related feedback may be visual, displayed along with (e.g., incorporated into) displayed images.

In some instances, the feedback may be configured to indicate or suggest outcome of the examination. For example, the manner in which visual feedback is provided (e.g., color thereof) may be adjusted to indicate if any issues are detected or suspected based on the strain-related measurements or calculations. Example use cases illustrating these features in the context of cervical strain elastography are shown and described with respect to FIGS. 3 and 4.

As noted above, in various implementations, various actions or functions performed during stain elastography related operations in accordance with the present disclosure may be done using artificial intelligence (AI). Example actions that may be processed and/or performed using by artificial intelligence (AI) related resources in the system may include: analysis of all strain values (e.g., within a selected measurement ROI-box); identification of the mean strain values and their location; identification of the upper percentile strain maxima and their location; identification of the lower percentile strain minima and their location; exclusion of the mean areas; calculation of the strain ratio of hard to soft; display of the hard, soft, and ratio values; etc.

Figure 3:
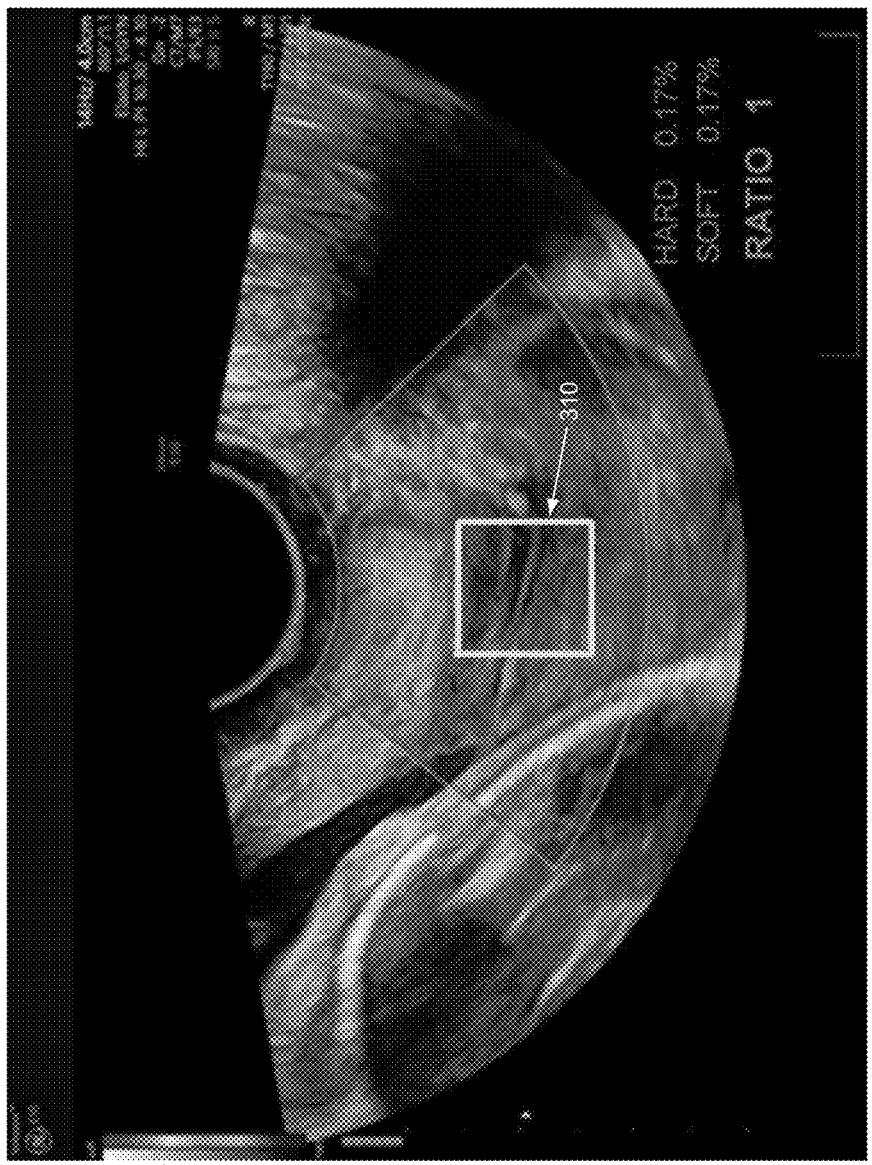
FIG. 3 illustrates example image generated in an example medical imaging system configured for supporting automatic measurement of strains and strain-ratio calculation for sonoelastography.

FIG. 3 illustrates example image generated in an example medical imaging system configured for supporting automatic measurement of strains and strain-ratio calculation for sonoelastography. Shown in FIG. 3 is a screenshot of an image 300 (e.g., ultrasound image) generated in a medical imaging system (e.g., ultrasound system 200 of FIG. 2).

The ultrasound image 300 may correspond to one of ultrasound images of a cervix and surrounding area generated and displayed in a system implemented in accordance with the present disclosure, such as the ultrasound system 200 of FIG. 2. In particular, the ultrasound image 300 illustrates example real-time visual feedback that may be provided during example use scenario of the ultrasound image 200 in the course of conducting strain sonoelastography of the cervix (to check for softening thereof).

In this regard, as explained above, during strain elastography the area being examined may be compressed/decompressed manually using the ultrasound probe. In the case of strain elastography of the cervix this be performed as endo-vaginal examination, using ultrasound probe configured for such examination. The compression/decompression produces strain of the tissues of the cervix and surrounding area, underneath the probe. The strain values may be automatically measured by the system (e.g., based on speckle based calculation, as described above with respect to FIG. 2), and the mean strain value may also be calculated by the system.

The system may also automatically assess the outcome of the examination based on the strain measurements. For example, the assessment may be based on determination of strain ratio of hard tissue to soft tissue. In this regard, assessing the calculated strain ratio may be based on pre-defined criteria and/or parameters—e.g., maxima (or minima) thresholds, such as based on measured strain, for determining when softness (or hardness) of tissue meets particular limits as to be considered soft (or hard) tissue. The assessment may be limited to particular area in the images, which may be specified by the user (clinician). For example, as shown in FIG. 3, the user may select the to-be-assessed area on the screen, by use of user-selected ROI-box 310 (e.g., using suitable user controls). In the context of strain elastography of the cervix, the clinician may select an area corresponding to and/or including the cervical canal and surrounding tissue.

The system may then provide feedback relating to the strain measurements and/or assessment based thereon. This may be done visually, such as by incorporating strain related feedback into the displayed images. For example, after measuring the strain values based on the ultrasound images (or data corresponding thereto), the system may identify location of areas (e.g., green) corresponding to or having mean strain values, identify location of areas (e.g., red) corresponding to upper percentile strain maxima (e.g., soft tissue), and identify location of areas (e.g., blue) corresponding to lower percentile strain minima (e.g., hard tissue). The system may then perform strain-ration calculations. In this regard, the system may exclude the mean areas (green), and calculate the strain ratio of hard (blue) to soft (red), and then provide feedback (e.g., display) relating to identified hard tissue, soft tissue, and calculated ratio values. In this regard, in some implementation, the manner in which feedback is provided (e.g., visually) may be configured to indicate the outcome of the assessment, such as based on predetermined criteria. For example, based on pre-defined cut-off values, for each specific application, the manner in which feedback regarding the ratio is provided (color used in displaying the ratio) may be adaptively adjusted.

For example, as shown in FIG. 3, tissue with higher strain values (softer) is colored red (with increasing color saturation); whereas tissue with lower strain values (harder) is colored blue (with increasing color saturation). The ratio of soft tissue to hard tissue within the user-selected ROI-box 310 is calculated and displayed. In this regard, the manner in which the calculated ratio is displayed may be configured to indicate the outcome of the assessment, based on pre-defined cut-off values for cervical strain assessment. For example, the color used in displaying the ratio may be configured to indicate whether the ratio, based on applicable cut-off value(s), suggests if softening of the cervix occurred or is occurring—e.g., green when ratio is within predefined acceptable limits, red if the ratio is not.

In the example use case illustrated in FIG. 3, for example, the ratio is 1 (as each of soft tissue and hard tissue within the ROI-box 310 is the same, at about 0.17%), which may be within acceptable limits. Thus, the word "Ratio" and calculated ratio value ("1") are displayed in green.

Figure 4:
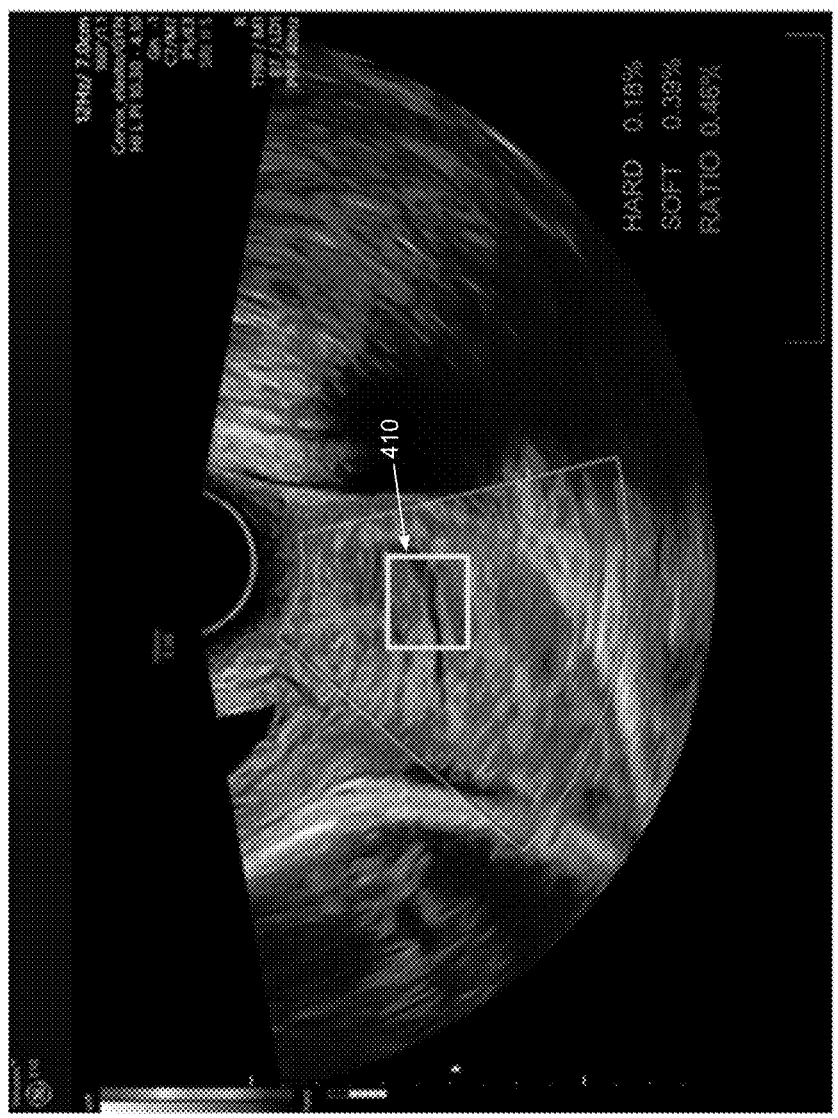
FIG. 4 illustrates example image generated in an example medical imaging system configured for supporting automatic measurement of strains and strain-ratio calculation for sonoelastography.

FIG. 4 illustrates example image generated in an example medical imaging system configured for supporting automatic measurement of strains and strain-ratio calculation for sonoelastography. Shown in FIG. 4 is a screenshot of an image 400 (e.g., ultrasound image) generated in a medical imaging system (e.g., ultrasound system 200 of FIG. 2).

The image 400 may be generated in the same manner as image 300, as described with respect to FIG. 3—that is, in the course of strain elastography of the cervix using a system implemented in accordance with the present disclosure (e.g., ultrasound system 200 of FIG. 2), with the system being configured to make automatic strain related measurements and calculations, and assessments based thereon, particularly with respect to softening of the cervix. In the example use case illustrated in FIG. 4, however, the ratio (hard tissue to soft tissue) is calculated to be 0.46%, as soft tissue within a user-selected ROI-box 410 (e.g., including the cervical canal and surrounding area), as determined in the system based on automatic strain measurement and applicable softness criteria constitutes 0.39% of the area enclosed in the ROI-box 410, whereas hard tissue within the ROI-box 410, as determined in the system based on automatic strain measurement and applicable hardness criteria constitutes 0.18%.

As a ratio of 0.46% may exceed (or fall below) acceptable limits, the feedback may be provided differently than in the example use scenario illustrated in FIG. 3. Thus, as shown in FIG. 4, the word "Ratio" and calculated ratio value ("0.46%") are displayed in green.

Figure 5:
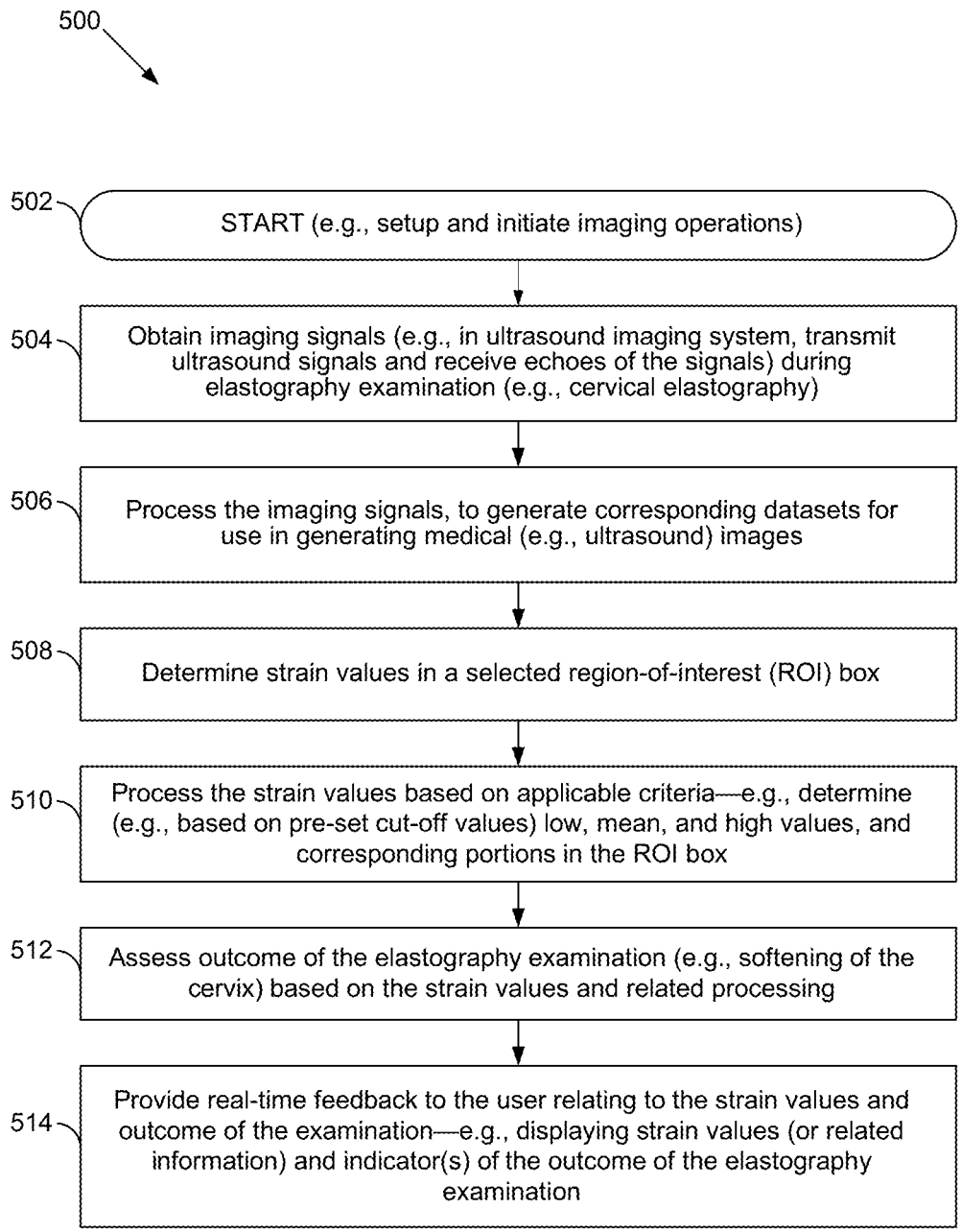
FIG. 5 illustrates a flowchart of an example steps that may be performed for ultrasound imaging with automatic measurement of strains and strain-ratio calculation for sonoelastography.

FIG. 5 illustrates a flowchart of an example steps that may be performed for ultrasound imaging with automatic measurement of strains and strain-ratio calculation for sonoelastography.

Shown in FIG. 5 is flow chart 500, comprising a plurality of example steps (represented as blocks 502-514), which may be performed in a suitable medical imaging system (e.g., the ultrasound system 200 of FIG. 2) for performing elastography with automatic measurement of strains and strain-ratio calculation.

In start step 502, the system may be setup, and operations may initiate.

In step 504, imaging signals may be obtained during elastography examination (e.g., cervical elastography). For example, in an ultrasound imaging system, this may comprise transmitting ultrasound signals and receiving corresponding echoes of the signals.

In step 506, the imaging signals (e.g., received echoes of the ultrasound signals) may be processed, to generate corresponding datasets for use in generating corresponding medical images (e.g., ultrasound images).

In step 508, strain values in a selected region-of-interest (ROI) box may be determined. In this regard, the ROI-box may be user-selected, such as via interaction with a display unit of the system. The strain values may be determined, for example, based on calculations based on speckle correlation of the signals of compressed vs. uncompressed tissue, as described above.

In step 510, the strain values may be processed, using AI-algorithms implemented in the system, such as based on applicable criteria. For example, processing the strain values may comprise determining (e.g., based on pre-set cut-off values) low, mean, and high values, and corresponding portions in the ROI box. This may allow, for example, identify tissue that may be assessed as being soft, hard, or in-between.

In step 512, outcome of the elastography examination (e.g., softening of the cervix) may be assessed based on the strain values and related processing. For example, in the context of cervical examination, softening of the cervix may be assess based on ratio of hard tissue to soft tissue within the ROI-box.

In step 514, real-time feedback relating to the strain values, related calculations, and/or outcome of the examination may be provided to the user. For example, this may comprise displaying strain values (or relate information) and indicator(s) of the outcome of the elastography examination.

An example method, in accordance with the present disclosure, for elastography based examination with automatic measurement of strains and strain-ratio calculation comprises processing, by at least one processor, imaging data obtained during elastography examination of a patient, with the imaging data corresponding to a particular medical imaging technique; generating, by the at least one processor, based on processing of the imaging data, corresponding one or more medical images; calculating strain values corresponding to a region-of-interest (ROI) within the one or more medical images, processing the calculated strain values, with the processing comprising determining based on the elastography examination, a plurality of ranges corresponding to the calculated strain values, identifying portions of the region-of-interest (ROI) corresponding to each of the plurality of ranges, and assessing an outcome of the elastography examination based on one or more of: the calculated strain values, the plurality of ranges, and the portions of the region-of-interest (ROI); and providing, based on the processing of the calculated strain values, strain related feedback.

In an example implementation, the method further comprises processing the calculated strain values via the at least one processor automatically using one or more artificial intelligence based algorithms.

In an example implementation, the method further comprises processing the calculated strain values based on a type of the elastography examination. The type of the elastography examination may comprise one of cervical elastography, prostate elastography, breast elastography, and thyroid elastography.

In an example implementation, the method further comprises determining the plurality of ranges based on one or more pre-set cut off values.

In an example implementation, the method further comprises determining the one or more pre-set cut off values based on a type of the elastography examination.

In an example implementation, the plurality of ranges comprises at least a low range, a high range, and a mean range, and providing the strain related feedback comprises displaying strain values for at least of the high range and the low range in at least one displayed medical image of the one or more medical images.

In an example implementation, assessing the outcome of the elastography examination comprises calculating a ratio between the high range and the low range.

In an example implementation, providing the strain related feedback comprises providing feedback relating to the outcome of the elastography examination.

In an example implementation, providing feedback relating to the outcome of the elastography examination comprises displaying an indicator of the outcome of the elastography examination in at least one displayed medical image of the one or more medical images.

In an example implementation, where the elastography examination comprises cervical elastography, the outcome of the elastography examination comprises softening of a cervix of the patient.

In an example implementation, providing the strain related feedback comprises providing feedback indicating a risk for preterm delivery based on determination that softening of the cervix occurred or is occurring.

In an example implementation, the medical imaging technique comprises ultrasound imaging, and the medical images comprise ultrasound images generated based on received echo ultrasound signals.

An example system, in accordance with the present disclosure, for elastography based examination with automatic measurement of strains and strain-ratio calculation comprises: a scanning device configured to obtaining imaging signals during elastography examination of a patient, with the imaging data corresponding to a particular medical imaging technique; a display device configured to display images; and at least one processor configured to: process the imaging data obtained via the scanner device; generate based on processing of the imaging data, corresponding one or more medical images; display via the display device, the one or more medical images; automatically, using one or more artificial intelligence based algorithms: calculate strain values corresponding to a region-of-interest (ROI) within at least one of the one or more medical images, and process the calculated strain values, with the processing comprising: determining based on the elastography examination, a plurality of ranges corresponding to the calculated strain values, identifying portions of the region-of-interest (ROI) corresponding to each of the plurality of ranges, and assessing an outcome of the elastography examination based on one or more of: the calculated strain values, the plurality of ranges, and the portions of the region-of-interest (ROI); and provide, based on the processing of the calculated strain values, strain related feedback.

In an example implementation, the at least one processor is further configured to process the calculated strain values based on a type of the elastography examination.

In an example implementation, the at least one processor is further configured to determine the plurality of ranges based on one or more pre-set cut off values.

In an example implementation, the at least one processor is further configured to determine the one or more pre-set cut off values based on a type of the elastography examination.

In an example implementation, the plurality of ranges comprises at least a low range, a high range, and a mean range, and the at least one processor is further configured to display via the display device, strain values for at least of the high range and the low range in at least one displayed medical image of the one or more medical images.

In an example implementation, the at least one processor is further configured to, when assessing the outcome of the elastography examination, calculate a ratio between the high range and the low range.

In an example implementation, providing the strain related feedback comprises providing feedback relating to the outcome of the elastography examination, and the at least one processor is further configured to display via the display device, when providing the strain related feedback, an indicator of the outcome of the elastography examination in at least one displayed medical image of the one or more medical images.

In an example implementation, the elastography examination comprises cervical elastography, the outcome of the elastography examination comprises softening of a cervix of the patient of, and the at least one processor is further configured to, when providing the strain related feedback, provide an indicator of a risk for preterm delivery based on determination that softening of the cervix occurred or is occurring.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method comprising:
    processing, by at least one processor, imaging data obtained during elastography examination of a patient, wherein the imaging data correspond to a particular medical imaging technique;
    generating, by the at least one processor, based on processing of the imaging data, corresponding one or more medical images;
    calculating strain values corresponding to a region-of-interest (ROI) within the one or more medical images;
    processing the calculated strain values, wherein the processing comprises:
        determining based on the elastography examination, a plurality of ranges corresponding to the calculated strain values;
        identifying portions of the region-of-interest (ROI) corresponding to each of the plurality of ranges; and
        assessing an outcome of the elastography examination based on one or more of: the calculated strain values, the plurality of ranges, and the portions of the region-of-interest (ROI); and
    providing, based on the processing of the calculated strain values, strain related feedback;
    wherein the elastography examination comprises cervical elastography, and wherein the outcome of the elastography examination comprises examining softening of a cervix of the patient.

2. The method of claim 1, further comprising processing the calculated strain values via the at least one processor automatically using one or more artificial intelligence based algorithms.

3. The method of claim 1, further comprising processing the calculated strain values based on a type of the elastography examination.

4. The method of claim 3, wherein the type of the elastography examination comprises one of cervical elastography, prostate elastography, breast elastography, and thyroid elastography.

5. The method of claim 1, comprising determining the plurality of ranges based on one or more pre-set cut off values.

6. The method of claim 5, comprising determining the one or more pre-set cut off values based on a type of the elastography examination.

7. The method of claim 1, wherein the plurality of ranges comprises at least a low range, a high range, and a mean range, and wherein providing the strain related feedback comprises displaying strain values for at least one of the high range and the low range in at least one displayed medical image of the one or more medical images.

8. The method of claim 1, wherein the plurality of ranges comprises at least a low range, a high range, and a mean range, and wherein assessing the outcome of the elastography examination comprises calculating a ratio between the high range and the low range.

9. The method of claim 1, wherein providing the strain related feedback comprises providing feedback relating to the outcome of the elastography examination.

10. The method of claim 9, wherein providing feedback relating to the outcome of the elastography examination comprises displaying an indicator of the outcome of the elastography examination in at least one displayed medical image of the one or more medical images.

11. The method of claim 1, wherein providing the strain related feedback comprises providing feedback indicating a risk for preterm delivery based on a determination that softening of the cervix occurred or is occurring.

12. The method of claim 1, wherein the medical imaging technique comprises ultrasound imaging, and wherein the medical images comprise ultrasound images generated based on received echo ultrasound signals.

13. A system comprising:
    a scanning device configured to obtaining imaging signals during elastography examination of a patient, wherein the imaging data correspond to a particular medical imaging technique;
    a display device configured to display images; and
    at least one processor configured to:
        process the imaging data obtained via the scanner device;
        generate based on processing of the imaging data, corresponding one or more medical images;
        display via the display device, the one or more medical images;
        automatically, using one or more artificial intelligence based algorithms:
            calculate strain values corresponding to a region-of-interest (ROI) within at least one of the one or more medical images;
            process the calculated strain values, wherein the processing comprises:
                determining based on the elastography examination, a plurality of ranges corresponding to the calculated strain values;
                identifying portions of the region-of-interest (ROI) corresponding to each of the plurality of ranges; and
                assessing an outcome of the elastography examination based on one or more of: the calculated strain values, the plurality of ranges, and the portions of the region-of-interest (ROI); and
            provide, based on the processing of the calculated strain values, strain related feedback; and wherein:
the elastography examination comprises cervical elastography,
the outcome of the elastography examination comprises examining softening of a cervix of the patient of, and
the at least one processor is configured to, when providing the strain related feedback, provide an indicator of a risk for preterm delivery based on a determination that softening of the cervix occurred or is occurring.

14. The system of claim 13, wherein the at least one processor is configured to process the calculated strain values based on a type of the elastography examination.

15. The system of claim 13, wherein the at least one processor is configured to determine the plurality of ranges based on one or more pre-set cut off values.

16. The system of claim 15, wherein the at least one processor is configured to determine the one or more pre-set cut off values based on a type of the elastography examination.

17. The system of claim 13, wherein the plurality of ranges comprises at least a low range, a high range, and a mean range, and wherein the at least one processor is configured to display via the display device, when providing the strain related feedback, strain values for at least one of the high range and the low range in at least one displayed medical image of the one or more medical images.

18. The system of claim 13, wherein the plurality of ranges comprises at least a low range, a high range, and a mean range, and wherein the at least one processor is configured to, when assessing the outcome of the elastography examination, calculate a ratio between the high range and the low range.

19. The system of claim 13, wherein providing the strain related feedback comprises providing feedback relating to the outcome of the elastography examination, and wherein the at least one processor is configured to display via the display device, when providing the strain related feedback, an indicator of the outcome of the elastography examination in at least one displayed medical image of the one or more medical images.

20. A method comprising:
processing, by at least one processor, imaging data obtained during elastography examination of a patient, wherein the imaging data correspond to a particular medical imaging technique;
generating, by the at least one processor, based on processing of the imaging data, corresponding one or more medical images;
calculating strain values corresponding to a region-of-interest (ROI) within the one or more medical images;
processing the calculated strain values, wherein the processing comprises:
determining based on the elastography examination, a plurality of ranges corresponding to the calculated strain values;
identifying portions of the region-of-interest (ROI) corresponding to each of the plurality of ranges; and
assessing an outcome of the elastography examination based on one or more of: the calculated strain values, the plurality of ranges, and the portions of the region-of-interest (ROI); and
providing, based on the processing of the calculated strain values, strain related feedback;
wherein the plurality of ranges comprises at least a low range, a high range, and a mean range, and wherein providing the strain related feedback comprises displaying strain values for at least one of the high range and the low range in at least one displayed medical image of the one or more medical images.

21. A system comprising:
a scanning device configured to obtaining imaging signals during elastography examination of a patient, wherein the imaging data correspond to a particular medical imaging technique;
a display device configured to display images; and
at least one processor configured to:
process the imaging data obtained via the scanner device;
generate based on processing of the imaging data, corresponding one or more medical images;
display via the display device, the one or more medical images;
automatically, using one or more artificial intelligence based algorithms:
calculate strain values corresponding to a region-of-interest (ROI) within at least one of the one or more medical images;
process the calculated strain values, wherein the processing comprises:
determining based on the elastography examination, a plurality of ranges corresponding to the calculated strain values;
identifying portions of the region-of-interest (ROI) corresponding to each of the plurality of ranges; and
assessing an outcome of the elastography examination based on one or more of: the calculated strain values, the plurality of ranges, and the portions of the region-of-interest (ROI); and
provide, based on the processing of the calculated strain values, strain related feedback; and
wherein:
the plurality of ranges comprises at least a low range, a high range, and a mean range, and
the at least one processor is configured to display via the display device, when providing the strain related feedback, strain values for at least one of the high range and the low range in at least one displayed medical image of the one or more medical images.

* * * * *